US00PP28067P3

(12) United States Plant Patent
Suphachadiwong

(10) Patent No.: US PP28,067 P3
(45) Date of Patent: May 30, 2017

(54) ***VANDA* PLANT NAMED 'SPCDW1401'**

(50) Latin Name: ***Vanda* hybrid**
Varietal Denomination: SPCDW1401

(71) Applicant: Thumrong Suphachadiwong, Bangphra (TH)

(72) Inventor: Thumrong Suphachadiwong, Bangphra (TH)

(73) Assignee: Suphatchatwong Innovation Co., Ltd., Bangphra (TH)

( * ) Notice: Subject to any disclaimer, the term of this patent is extended or adjusted under 35 U.S.C. 154(b) by 6 days.

(21) Appl. No.: 14/756,327

(22) Filed: Aug. 27, 2015

(65) Prior Publication Data

US 2016/0066492 P1 Mar. 3, 2016

(30) Foreign Application Priority Data

Aug. 28, 2014 (QZ) ..... PBR 2014/2100

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — June Hwu
(74) *Attorney, Agent, or Firm* — Samuel R. McCoy, Jr.

(57) ABSTRACT

A new and distinct *Vanda* cultivar named 'SPCDW1401' which is characterized by unique sepal and petal coloration of dark, slightly purplish-red (sangria color) against a background coloration which is a combination of a lighter shade of sangria and dark vanilla, dark red spotting on the dorsal sepal and lateral petals, a netting pattern of the lateral sepals towards the center of the flower, and lateral sepals that are heavily blotched dark red. The margins of all petals and sepals are slightly ruffled. The new variety is a *Vanda*, typically produced as an indoor ornamental plant.

3 Drawing Sheets

Latin name of the genus and species: The Latin name of the genus and species of the novel variety disclosed herein is *Vanda* hybrid.

Variety denomination: The inventive variety of *Vanda* disclosed herein has been given the variety denomination 'SPCDW1401'.

CROSS REFERENCE TO RELATED APPLICATIONS

This application claims priority to the Community Plant Variety Rights application number 2014/2100, filed Aug. 28, 2014, which is herein incorporated by reference.

BACKGROUND OF THE INVENTION

Parentage: The *Vanda* variety 'SPCDW1401' is the result of a planned breeding program. The new variety originated as a seedling from the crossing of the unpatented, proprietary seed parent *Vanda* 'RCB' with the unpatented, proprietary pollen parent referred to as *Vanda* 'D2N'. The crossing was made by the inventor in his research greenhouse in Chonburi, Thailand in October of 2000.

The new variety was first selected by the inventor, Thumrong Suphachadiwong, a citizen of Thailand, in February of 2006, in a research greenhouse belonging to the inventor in Chonburi, Thailand. After identifying the new variety as a potentially interesting selection, the inventor continued confidential testing and propagation of 'SPCDW1401', assessing stability of the unique characteristics of this variety.

Asexual Reproduction: Asexual reproduction of the new cultivar 'SPCDW1401' was first performed at a commercial laboratory belonging to the inventor in Chonburi, Thailand by tissue culture in September of 2008. Access to all plants was restricted, as plants were kept in a greenhouse not open to the public, and tissue culture plantlets were in a laboratory belonging to the inventor, and not accessible to the public. Through subsequent propagation by vegetative cuttings, multiple generations have been reproduced, which have shown that the unique features of this cultivar are stable and reproduced true to type.

SUMMARY OF THE INVENTION

The cultivar 'SPCDW1401' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1401'. These characteristics in combination distinguish 'SPCDW1401' as a new and distinct *Vanda* cultivar:

1. *Vanda* 'SPCDW1401' exhibits unique sepal and petal coloration of dark, slightly purplish-red (sangria color) against a background coloration which is a combination of a lighter shade of sangria and dark vanilla; and,
2. *Vanda* 'SPCDW1401' exhibits unique patterning of the sepals and petals; specifically, dark red spotting of the dorsal sepal and lateral petals, and netting of the lateral sepals towards the center of the flower, and lateral sepals that are heavily blotched dark red; and,
3. *Vanda* 'SPCDW1401' exhibits sepal and petal margins which are slightly ruffled.

BOTANICAL DESCRIPTION OF THE PLANT

Figure 1:
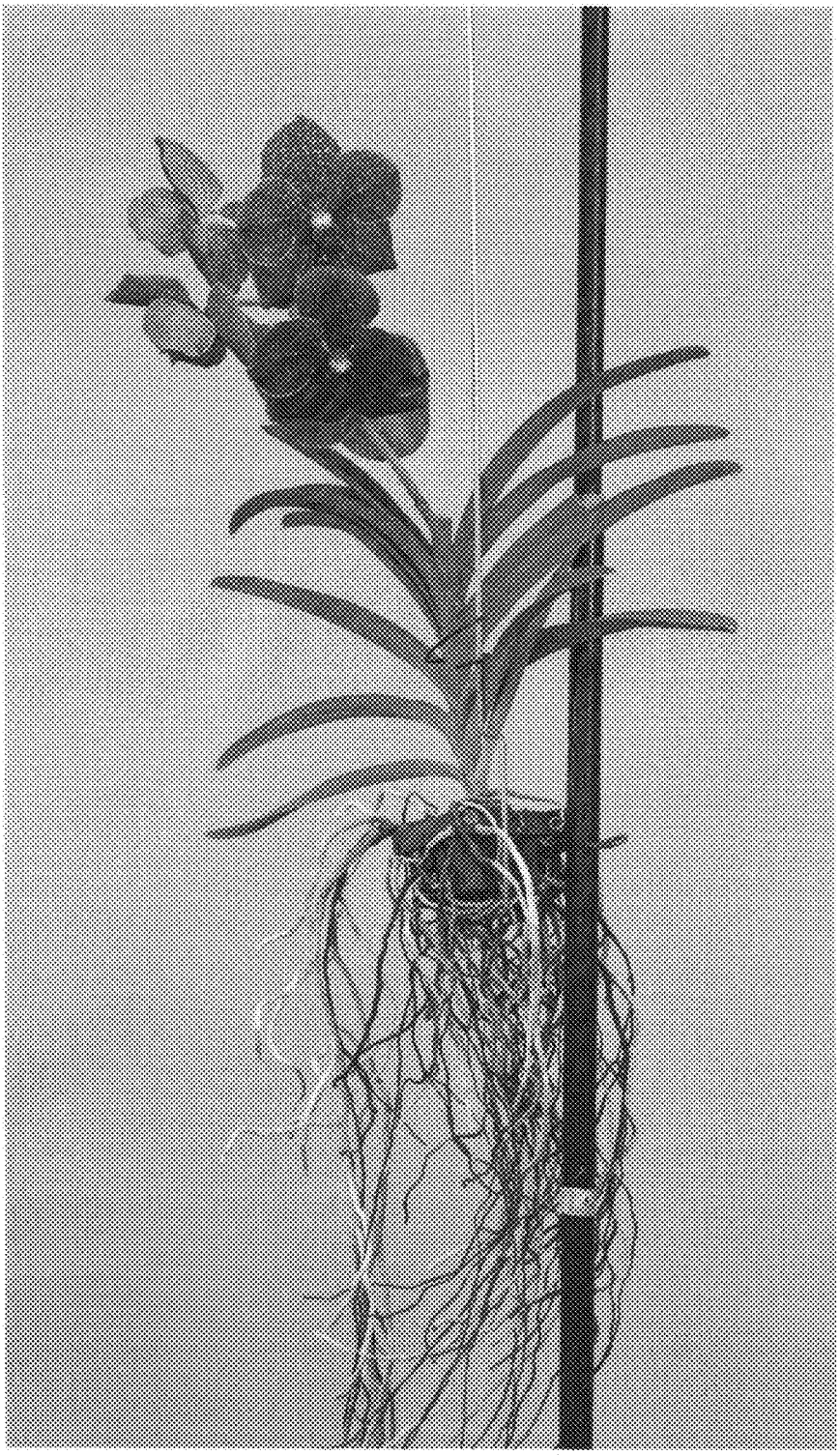
FIG. 1 illustrates, as nearly true as it is reasonably possible to make the same in color photographs of this type, an exemplary plant of 'SPCDW1401' grown in a commercial greenhouse in Honselersdijk, the Netherlands. This plant is approximately 5 years old, shown planted in an 8 by 8 cm container.
Figure 2:
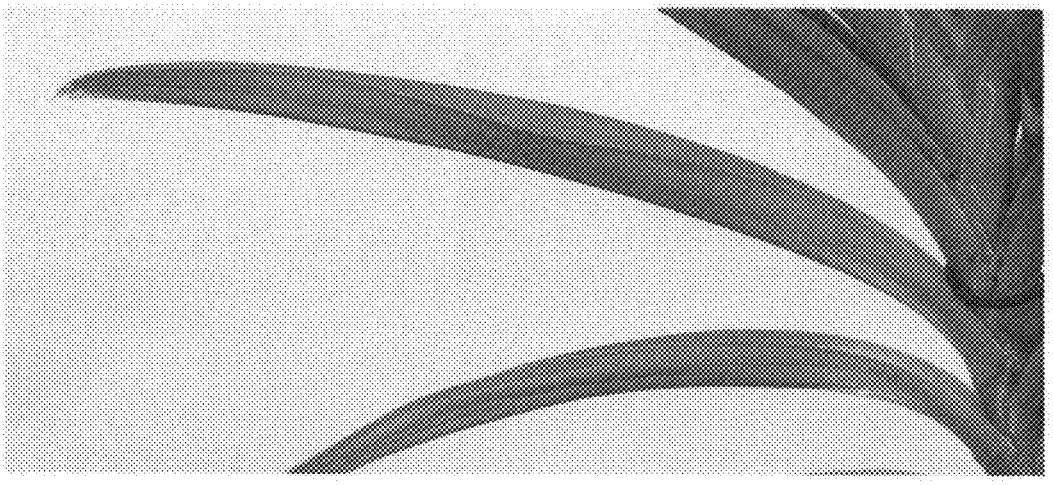
FIG. 2 illustrates, as nearly true as it is reasonably possible to make the same in color photographs of this type, the typical foliage of 'SPCDW1401'.
Figure 3:
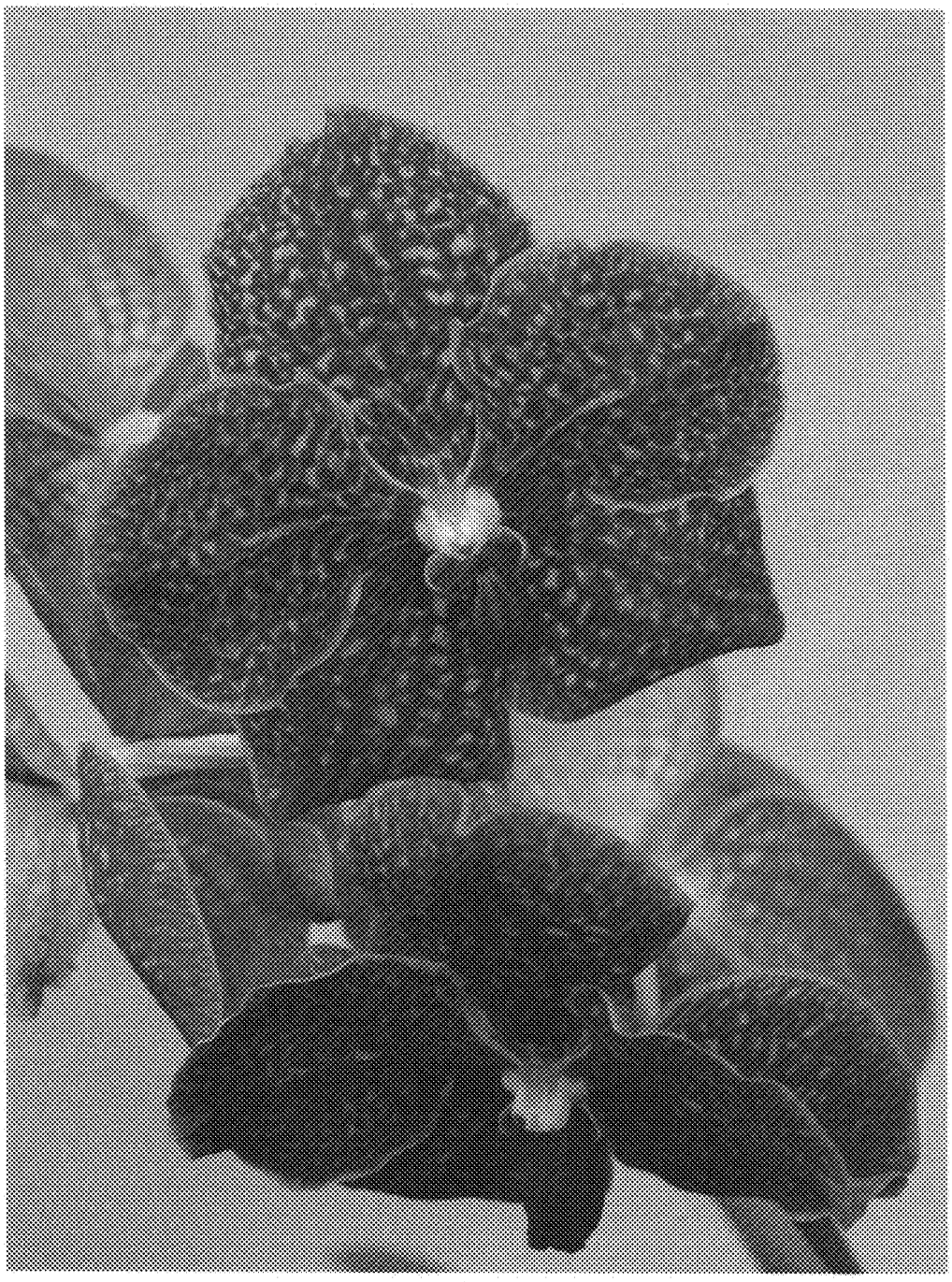
FIG. 3 illustrates, as nearly true as it is reasonably possible to make the same in color photographs of this type, the typical flowers of 'SPCDW1401'.

The following observations and measurements describe 'SPCDW1401' plants grown in a greenhouse in Honselersdijk, the Netherlands. Temperatures ranged were approximately 23 degrees Celsius during the day and 19 degrees Celsius at night. No photoperiodic or chemical treatments were given to the plants. When natural lighting fell below 150 Watt, artificial lighting is given at 10,000 lux for 16 hours a day.

Those skilled in the art will appreciate that certain characteristics will vary with older or, conversely, with younger plants. 'SPCDW1401' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2007 (fifth edition).

A botanical description of 'SPCDW1401' and comparisons with other varieties of *Vanda* are provided below.

Plant description:

- *Growth habit*.—Monopodial, upright.
- *Average height from base (plant grown in hanging basket, so no soil line present) to top of foliage*.—28.4 cm.
- *Average height from base (plant grown in hanging basket, so no soil line present) to top of flowers*.—45.0 cm.
- *Plant spread*.—Average of 46.8 cm.
- *Normal pot size*.—Hanging basket (8 by 8 cm, square).
- *Growth rate*.—Moderate.
- *Propagation type*.—Meristematic tissue culture propagation using the base of the leaves.
- *Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease resistance*.—Good resistance to the normal diseases found in *Vanda*.
- *Drought tolerance and cold tolerance*.—Drought tolerance is typical for species. Superior cold tolerance, to approximately 6 degrees Celsius.

Root system:

- *General*.—Moderate to heavy rooting with aerial roots only located at the base of the stem, growing from approximately the lowest 27.5 percent of the stem. Roots very fleshy, non-fibrous. Mature roots becoming woody and inactive.
- *Diameter, juvenile roots*.—0.4 cm, on average.
- *Dimensions, mature roots*.—33.5 cm long with a diameter of 0.3 cm, on average.
- *Color, root apex*.—Yellow-Green RHS 152A.
- *Color, juvenile roots*.—Greyed-Green RHS 192C to 192D.
- *Color, mature roots*.—Yellow-Green RHS 146C to 146D.

Foliage:

- *Arrangement*.—Distichous.
- *Quantity*.—16 leaves, on average.
- *Dimensions*.—23.3 cm long and 2.2 cm wide, on average.
- *Shape of blade*.—Ligulate, strongly carinate.
- *Aspect*.—Slightly curved.
- *Apex*.—Unequal praemorse.
- *Base*.—Sheathing.
- *Sheath dimensions*.—1.7 cm long ad 1.4 cm wide, on average.
- *Sheath color*.—Yellow-Green RHS N144A.
- *Margin*.—Entire.
- *Texture of top surface*.—Glabrous, matte.
- *Texture of bottom surface*.—Glabrous, matte.
- *Color*.—Juvenile foliage, adaxial surface — Green RHS 143B, slightly darker toward the margins, near Green RHS 143A. Juvenile foliage, abaxial surface — Approximates to a combination of Green RHS 143A and Yellow-Green RHS 144A. Mature foliage, adaxial surface — Yellow-Green RHS 144A and Green RHS 143A at a near the margins. Mature foliage, abaxial surface — Yellow-Green RHS 144A.
- *Venation*.—Parallel.
- *Venation coloration*.—Yellow-Green RHS 144A on both the adaxial and abaxial surfaces.
- *Petiole*.—No petioles present, leaves sessile.

Inflorescence:

- *Flowers per stem*.—Average of 6.
- *Inflorescence arrangement*.—Axially placed raceme.
- *Inflorescence height*.—Approximately 22.0 cm (measured from base of lowest flower to top of upper flower).
- *Inflorescence width*.—Approximately 19.5 cm.
- *Peduncle*.—Length — Approximately 25.3 cm. Width — Approximately 0.6 cm. Aspect — Approximately 20° angle to rosette. Strength — Strong. Texture — Smooth, moderately glossy. Color — Yellow-Green RHS 144B.

Bud:

- *Rate of opening*.—Buds open approximately three weeks from first sight.
- *Length*.—Average of 1.4 cm.
- *Diameter*.—Average of 1.3 cm.
- *Shape*.—Broad obovate.
- *Color*.—Purple RHS 75D, with intonations of Red-Purple RHS 60D at the apex and intonations of Purple-Violet RHS N8OB elsewhere on the bud.

Flower:

- *Flower type*.—Zygomorphic (orchidaceous), typical shape for the genus *Vanda*.
- *Shape*.—Zygomorphic, consisting of three sepals and three petals, one of which is transformed into a labellum; the two lateral petals slightly overlapping the dorsal sepal and moderately overlapping the lateral sepals; lateral sepals moderately overlap one another.

*Length* (*height*).—Approximately 10.9 cm.

*Width*.—Approximately 9.9 cm.

*Depth*.—Approximately 3.2 cm.

*Fragrance*.—No fragrance.

*Persistent*.—No.

*Lastingness of flowers*.—Individual flowers can persist on the inflorescence for up to 6 weeks, counted from the day of opening until the day the flower drops.

*Quantity of petals*.—3; two conventional petals and one labellum.

*Petals*.—Arrangement — One lateral petal on each side. Length — Approximately 5.0 cm. Width — Approximately 5.0 cm. Shape — Near orbicular to reniform. Apex — Obtuse. Base — Cuneate. Margin — Entire; slightly undulated. Texture of upper forward surface — Glabrous, matte, velvety. Texture of lower back surface — Glabrous, matte, velvety. Color when opening, forward surface — A combination of Greyed-Red RHS 182C to 182D and Greyed-Purple RHS 185B, 185C and 187D; heavily dotted with Greyed-Purple RHS 183A and N186C. Color when opening, back surface — Greyed-Green RHS 195C to 195D. Color when fully opened, forward surface — A combination of Greyed-Red RHS 182C to 182D and Greyed-Purple RHS 185B, 185C and 187D; heavily dotted with Greyed-Purple RHS 183A and N186C. Color when fully opened, back surface — Greyed-Green RHS 195C to 195D. Fading, forward surface — Not fading. Fading, back surface — Not fading. Venation — Reticulate. Venation color, fully opened, forward surface — Main vein is Red-Purple RHS 61A to Greyed-Purple 187D. Other veins are the same color as the petal; that is, not distinguishable from the petal. Venation color, fully opened, back surface — Main vein is Purple RHS N78B to N78C; other veins are Red-Purple RHS 71B to 71C.

*Labellum*.—Shape — Three-lobed; the shape of the lateral lobes is reniform, and the aspect is involute; the shape of the central lobe is ovate, and the aspect is slightly revolute. Length — Overall length — Approximately 2.1 cm. Central lobe — Approximately 1.9 cm. Lateral lobes — Approximately 1.0 cm. Width — Overall width — Approximately 1.6 cm. Central lobe — Approximately 1.1 cm. Lateral lobes — Approximately 0.8 cm. Apex — Central lobe — Emarginate. Lateral lobes — Obtuse. Base — Central lobe — Cuneate. Lateral lobes — Cuneate. Margin — Central lobe — Entire; moderately undulated. Lateral lobes — Entire; not undulate. Texture and luster of upper surface — Central lobe — Glabrous, velvety, and slightly glossy; 3 callosities present. Lateral lobes — Glabrous, velvety, and slightly glossy. Texture and luster of lower surface — Central lobe — Glabrous, velvety, and matte. Lateral lobes — Glabrous, velvety, and matte. Color when opening, forward surface — Central lobe — Near Greyed-Purple RHS N186C and darker toward the apex, near Greyed-Purple RHS N186A and Greyed-Purple RHS N186B. Callosities are near Red-Purple RHS 59B. Lateral lobes — Near Purple RHS N77B, dotted with Red-Purple RHS 64A; apex is near Yellow RHS 11A; base is near Yellow-Orange RHS 17A. Color when opening, back surface — Central lobe — Near Greyed-Purple RHS N186C and darker toward the apex, near Greyed-Purple RHS N186B. Lateral lobes — Near Greyed-Green RHS 195B and striped with Red-Purple RHS 60B and 60C toward the base; intonations of Yellow RHS 12C. Color when fully opened, forward surface — Central lobe — Near Greyed-Purple RHS N186C and darker toward the apex, near Greyed-Purple RHS N186A and Greyed-Purple RHS N186B. Callosities are near Red-Purple RHS 59B. Lateral lobes — Near Purple RHS N77B, dotted with Red-Purple RHS 64A; apex is near Yellow RHS 11A; base is near Yellow-Orange RHS 17A. Color when fully opened, back surface — Central lobe — Near Greyed-Purple RHS N186C and darker toward the apex, near Greyed-Purple RHS N186B. Lateral lobes — Near Greyed-Green RHS 195B and striped with Red-Purple RHS 60B and 60C toward the base; intonations of Yellow RHS 12C. Fading, forward surface — Not fading Fading, back surface — Not fading Venation color, fully opened, forward surface — No venation visible on labellum. Venation color, fully opened, back surface — No venation visible on labellum.

*Spurs*.—Quantity — Average of 1. Appearance — Short triangular, in line with central lobe of labellum. Length — Approximately 0.7 cm. Width — Approximately 0.6 cm. Height — Approximately 0.5 cm, at the base. Shape — Short triangular. Apex — Obtuse. Base — Broad Cuneate. Margin — Entire. Texture — Glabrous, matte. Color — Greyed-White RHS 156C, striped with Greyed-Red RHS 182D.

*Sepals*.—Quantity — Average of 3. Appearance — One dorsal sepal (pointing upright) and two lateral sepals. Length — Dorsal sepal — Approximately 5.8 cm. Lateral sepal — Approximately 5.6 cm. Width — Dorsal sepal — Approximately 5.3 cm. Lateral sepal — Approximately 6.6 cm. Shape — Dorsal sepals are broad ovate and lateral sepals are reniform. Apex — Obtuse. Base — Cuneate. Margin — Entire. Texture — Glabrous, matte, velvety. Color, when opening and fully opened — Dorsal sepal, upper side — Yellow-White near RHS 158B and suffused with Greyed-Red near RHS 182C and 182D and Greyed-Purple RHS 185B and 185C; heavily dotted Greyed-Purple, in between RHS 183A and N186C. Dorsal sepal, under side — Greyed-Green near RHS 195C to 195D and very lightly suffused with Greyed-Red near RHS 182C and 182D and Greyed-Purple RHS 185B and 185C; lightly dotted Greyed-Purple, in between RHS 183A and N186C. Lateral sepal, upper side — Greyed-Yellow near RHS 161C and 162C, and suffused with Greyed-Red near RHS 182C and 182D and Greyed-Purple RHS 185B and 185C; netted and heavily blotched Greyed-Purple in between RHS 183A and 187A. Lateral sepal, under side — Greyed-Yellow RHS 162C and suffused with Greyed-Purple RHS 186B; netted and heavily blotched Greyed-Purple in between RHS 183A and 187A. Venation — Reticulate. Venation color, fully opened, forward surface — Main vein is Red-Purple RHS 60A to Greyed-Purple 187C. Other veins are the same color as the petal;

that is, not distinguishable from the petal. Venation color, fully opened, back surface — Main vein is Purple RHS N78B to N78C. On the dorsal sepal, other veins are Red-Purple RHS 72B. On lateral sepals, other veins are Red-Purple RHS 64A.

*Pedicels*.—Length — Approximately 5.5 cm. Diameter — Approximately 0.45 cm. Angle — Approximately 70° angle to peduncle. Strength — Very strong. Texture — Glabrous, axially angled with 5 "ribs", axially twisted (due to resupination), glossy. Color — Near White RHS N155B, with intonations of Purple RHS 75B and 75C near the distal end.

Reproductive organs:

*Stamens, style and stigma fused into column*?.—Yes.

*Column length*.—Approximately 0.5 cm.

*Column diameter*.—Approximately 0.8 cm.

*Column color*.—Yellow-White RHS 158B, with upper side striped Red-Purple RHS 73A.

*Ovary position*.—Inferior.

*Ovary diameter*.—Approximately 0.4 cm.

*Ovary color*.—White RHS N155B.

*Pollen color*.—Yellow-Orange RHS 14A.

Seed and fruit: No fruit and seed production has been detected to date.

Comparisons with the Parent Plants

Plants of the new cultivar 'SPCDW1401' are similar to the seed parent, *Vanda* 'RCB' in most horticultural characteristics. The new variety, however, produces larger flowers with a dark, slightly purplish-red general tonality, whereas the flowers of 'RCB' exhibit a lighter purple general tonality.

Plants of the new cultivar 'SPCDW1401' are similar to the pollen parent, *Vanda* 'D2N' in most horticultural characteristics. Plants of the new variety, however, are less compact with a longer leaf span than the pollen parent.

Comparisons with Similar *Vanda* Cultivars Known to the Inventor

'SPCDW1401' is similar in most horticultural characteristics to the commercial variety *Vanda* 'SPCDW1205' (U.S. Plant Pat. No. 26,322). However 'SPCDW1401' differs from 'SPCDW1205' in the following characteristics:

1. 'SPCDW1401' exhibits sepal and petal margins with a higher degree of ruffling compared to the sepal and petal margins of 'SPCDW1205'.
2. 'SPCDW1401' exhibits a dark, slightly purplish-red general tonality of the flower, whereas 'SPCDW1205' exhibits a greyed-purple general tonality of the flower.
3. The sepals of 'SPCDW1401' exhibit a netting pattern, whereas the sepals of 'SPCDW1205' lack said netting pattern.

That which is claimed is:

1. A new and distinct variety of *Vanda* plant named 'SPCDW1401', substantially as described and illustrated herein.

* * * * *